United States Patent
Kawashima et al.

(10) Patent No.: US 7,153,853 B2
(45) Date of Patent: *Dec. 26, 2006

(54) HETEROCYCLIC COMPOUNDS AND ANTITUMOR DRUGS CONTAINING THE SAME AS THE ACTIVE INGREDIENT

(75) Inventors: Seiichiro Kawashima, Tokyo (JP); Toshiyuki Matsuno, Tokyo (JP); Shinichi Yaguchi, Tokyo (JP); Yoshio Tsuchida, Tokyo (JP); Kenichi Saitoh, Tokyo (JP); Hiroya Sasahara, Tokyo (JP); Tetsuo Watanabe, Tokyo (JP)

(73) Assignee: Zenyaku Kogyo Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/532,245

(22) PCT Filed: Oct. 24, 2003

(86) PCT No.: PCT/JP03/13589

§ 371 (c)(1), (2), (4) Date: Apr. 22, 2005

(87) PCT Pub. No.: WO2004/037812

PCT Pub. Date: May 6, 2004

(65) Prior Publication Data
US 2006/0009440 A1 Jan. 12, 2006

(30) Foreign Application Priority Data
Oct. 25, 2002 (JP) .............................. 2002-311086

(51) Int. Cl.
C07D 413/14 (2006.01)
A61K 31/506 (2006.01)
A61K 31/5377 (2006.01)
A61P 35/00 (2006.01)

(52) U.S. Cl. ..................... 514/231.5; 544/112; 544/114

(58) Field of Classification Search ................ 544/112, 544/114; 514/231.5
See application file for complete search history.

(56) References Cited

U.S. PATENT DOCUMENTS 6,251,900 B1 6/2001 Kawashima et al.
2004/0116421 A1 6/2004 Kawashima et al.
2006/0009440 A1 1/2006 Kawashima et al.

FOREIGN PATENT DOCUMENTS

EP 1 020 462 7/2000
WO 00/43385 7/2000
WO 02/088112 11/2002

OTHER PUBLICATIONS

Cecil Textbook of Medicine, edited by Bennet, J.C., and Plum F., 20th edition, vol. 1, 1004-1010, 1996.*
Connor et al. Fundamental and Applied Toxicology vol. 30 (1): 93-101, 1996.*
Coley et al., Anticancer Research 16(4A); 1851-1855, 1996.*
U.S. Appl. No. 10/532,245, filed Apr. 22, 2005, Kawashima et al.
U.S. Appl. No. 11/404,078, filed Apr. 14, 2006, Yaguchi et al.

* cited by examiner

Primary Examiner—Venkataraman Balasubramanian
(74) Attorney, Agent, or Firm—Oblon, Spivak, McClelland, Maier & Neustadt, P.C.

(57) ABSTRACT

The present invention relates to heterocyclic compounds represented by the formula I

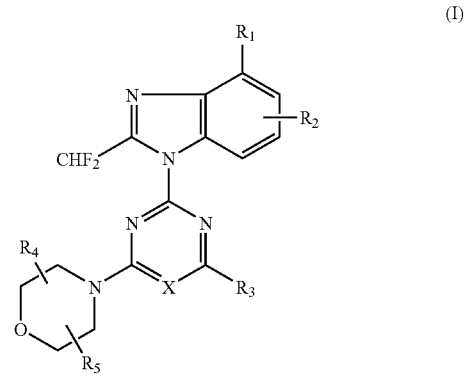

wherein X represents nitrogen atom or CH; $R_1$ represents halogen atom or hydroxyl; $R_2$ represents hydrogen atom, hydroxyl or amino; $R_3$ represents morpholino (which may be substituted with one or two $C_1$–$C_6$ alkyl), pyrrolidinyl (which may be substituted with hydroxy $C_1$–$C_6$ alkyl) or $NR_6R_7$ [$R_6$ represents $C_1$–$C_6$ alkyl and $R_7$ represents piperidinyl (which may be substituted with $C_1$–$C_6$ alkyl)]; $R_4$ and $R_5$ each represents hydrogen atom or $C_1$–$C_6$ alkyl, with the proviso that $R_2$ is hydrogen atom and $R_3$ is pyrrolidinyl (which may be substituted with hydroxy $C_1$–$C_6$ alkyl) when $R_1$ is hydroxyl

22 Claims, No Drawings

HETEROCYCLIC COMPOUNDS AND ANTITUMOR DRUGS CONTAINING THE SAME AS THE ACTIVE INGREDIENT

TECHNICAL FIELD

The present invention relates to heterocyclic compounds represented by the formula I or pharmaceutically acceptable salts thereof and antitumor agents containing the heterocyclic compounds as effective components:

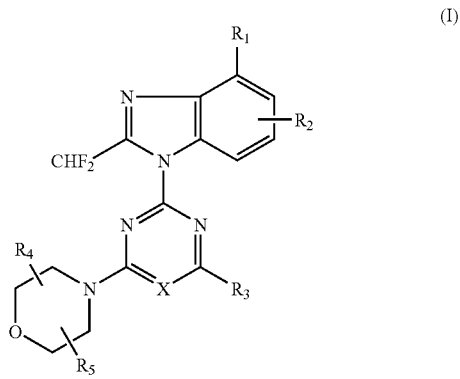

wherein X represents nitrogen atom or CH; $R_1$ represents halogen atom or hydroxyl; $R_2$ represents hydrogen atom, hydroxyl or amino; $R_3$ represents morpholino (which may be substituted with one or two $C_1$–$C_6$ alkyl), pyrrolidinyl (which may be substituted with hydroxy $C_1$–$C_6$ alkyl) or $NR_6R_7$ [$R_6$ represents $C_1$–$C_6$ alkyl and $R_7$ represents piperidinyl (which may be substituted with $C_1$–$C_6$ alkyl)]; $R_4$ and $R_5$ each represent hydrogen atom or $C_1$–$C_6$ alkyl, with the proviso that $R_2$ is hydrogen atom and $R_3$ is pyrrolidinyl (which may be substituted with hydroxy $C_1$–$C_6$ alkyl) when $R_1$ is hydroxyl.

BACKGROUND ART s-Triazine (1,3,5-triazine) and pyrimidine derivatives have been researched in the fields of synthetic resins, synthetic fibers, dyes and agricultural chemicals and a number of such compounds have been synthesized. In the field of pharmaceuticals, researches have been made with respect to antitumor, anti-inflammatory, analgesic, antispasmodic activities and the like. Especially, hexamethylmelamine (HMM) is well-known which has been developed as analogue of antitumor agent triethylenemelamine (TEM) [see, for example, B. L. Johnson et al. Cancer, 42: 2157–2161 (1978)].

TEM is known as alkylating agent and is an s-triazine derivative having cytotoxic antitumor activity. HMM has been marketed in Europe under the indications for the treatment of ovarian and small cell lung cancers, and its action on solid cancers have attractive.

Among the s-triazine derivatives, imidazolyl-s-triazine derivatives which exhibit cytotoxic and selective aromatase inhibitory activities have been proposed as medicine for estrogen-dependent diseases such as endometriosis, multicystic ovarium, mastosis, endometrium carcinoma and breast cancer (see, for example, PCT international publication WO93/17009).

In order to expand antitumor activities of HMM and to decrease aromatase inhibitory activities of imidazolyl-s-triazine derivatives, we, the inventors, carried out intensive studies to find out s-triazine and pyrimidine derivatives with substitution of benzimidazole (see, for example, PCT international publications WO99/05138 and WO00/43385).

However, there is still room for improvement on HMM with respect to its antitumor spectrum and intensity of antitumor activities against solid cancers in B. L. Johnson et al. Cancer, 42: 2157–2161 (1978). As to imidazolyl-s-triazine derivatives as disclosed in WO093/17009, they are limitative in application since they exhibit considerably higher aromatase inhibitory activities than their cytotoxic activities and application of them to cancerous patients other than those who suffer from estrogen-dependent diseases may lead to development of secondary effects such as menstrual disorders due to lack of estrogen. There are still, therefore, strong demands on medicines with no aromatase inhibitory activities and effective for solid cancers.

Even the compounds as disclosed in PCT international publications WO99/05138 and WO00/43385 have not been satisfactory with respect to their anti-tumor activities.

SUMMARY OF THE INVENTION

We, the inventors, further developed the studies to find out that heterocyclic compounds with specific substituents at position 2 of benzimidazole ring and represented by the formula I exhibit by far improved antitumor activities, thus completing the present invention.

The terms used for definition of letters in the formula I, by which the heterocyclic compounds of the present invention are represented, will be defined and exemplified in the following.

The term "$C_1$–$C_6$" refers to a group having 1 to 6 carbon atoms unless otherwise indicated.

The "$C_1$–$C_6$ alkyl" refers to a straight- or branched-chain alkyl group such as methyl, ethyl, n-propyl, isopropyl, n-butyl, tert-butyl, n-pentyl or n-hexyl.

The "hydroxy $C_1$–$C_6$ alkyl" refers to the above-mentioned "$C_1$–$C_6$ alkyl" with any of the carbon atoms coupled to hydroxy group.

The "halogen atom" refers to fluorine, chlorine, bromine or iodine.

The compounds according to the present invention may be as follows, though the present invention is not limited to these compounds.

2-(6-amino-4-chloro-2-difluoromethylbenzimidazol-1-yl)-4-(2,2-dimethylmorpholino)-6-morpholino-1,3,5-triazine 2-(6-amino-4-chloro-2-difluoromethylbenzimidazol-1-yl)-4-[methyl(1-methylpiperidin-4-yl)amino]-6-morpholino-1,3,5-triazine 2-(6-amino-4-chloro-2-difluoromethylbenzimidazol-1-yl)-4-(2-hydroxymethylpyrrolidin-1-yl)-6-morpholino-1,3,5-triazine 2-(4-chloro-2-difluoromethyl-5-hydroxybenzimidazol-1-yl)-4,6-dimorpholino-1,3,5-triazine 2-(4-chloro-2-difluoromethyl-5-hydroxybenzimidazol-1-yl)-4-(2,2-dimethylmorpholino)-6-morpholino-1,3,5-triazine 2-(2-difluoromethyl-4-hydroxybenzimidazol-1-yl)-4-(2-hydroxylmethylpyrrolidin-1-yl)-6-morpholino-1,3,5-triazine 2-(2-difluoromethyl-4-hydroxybenzimidazol-1-yl)-4-(2-hydroxylmethylpyrrolidin-1-yl)-6-morpholinopyrimidine 2-(6-amino-4-chloro-2-difluoromethylbenzimidazol-1-yl)-4-(2,2-dimethylmorpholino)-6-morpholinopyrimidine 2-(4-chloro-2-difluoromethyl-5-hydroxybezimidazol-1-yl)-4,6-dimorpholinopyrimidine 2-(4-chloro-2-difluoromethyl-5-hydroxybenzimidazol-1-yl)-4-(2,2-dimethylmorpholino)-6-morpholinopyrimidine 2-(4-bromo-2-difluoromethylbenzimidazol-1-yl)-4,6-dimorpholino-1,3,5-triazine 2-(4-fluoro-2-difluoromethylbenzimidazbl-1-yl)-4,6-dimorpholino-1,3,5-triazine The compounds of the present invention may have asymmetric carbon atoms in the structure. It is to be understood that isomers due to such asymmetric carbon atom or combination (racemate) of any of the isomers are included in the category of the compounds according to the present invention.

Furthermore, the compounds of the present invention may be in the form of pharmaceutically acceptable acid addition salts. The appropriate acid addition salts which can be used include, for example, inorganic salts such as hydrochloride, sulfate, hydrobromide, nitrate and phosphate as well as organic acid salts such as acetate, oxalate, propionate, glycolate, lactate, pyruvate, malonate, succinate, maleate, fumarate, malate, tartarate, citrate, benzoate, cinnamate, methanesulfonate, benzenesulfonate, p-toluenesulfonate and salicylate.

Production Processes

The compounds of the present invention represented by the formula I may be prepared by, as shown in the following reaction formula, reacting cyanuric chloride or 2,4,6-trichloropyrimidine (compound II) as starting material with benzimidazole compound (compound V), morpholine compound (compound VI) and $R_3H$ (compound VII) successively in the order named.

Reaction Formula

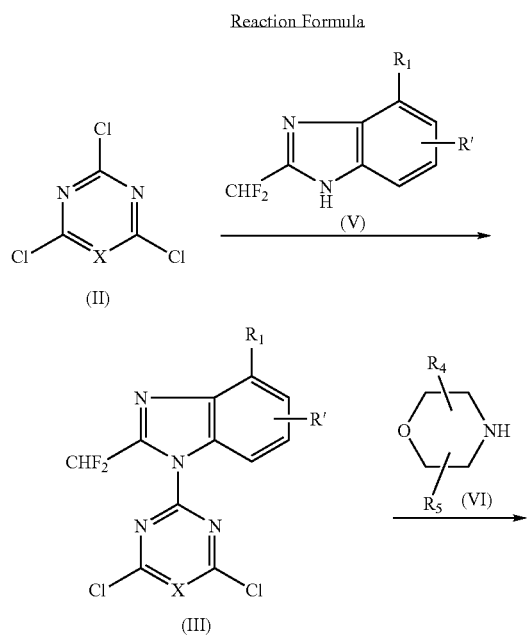

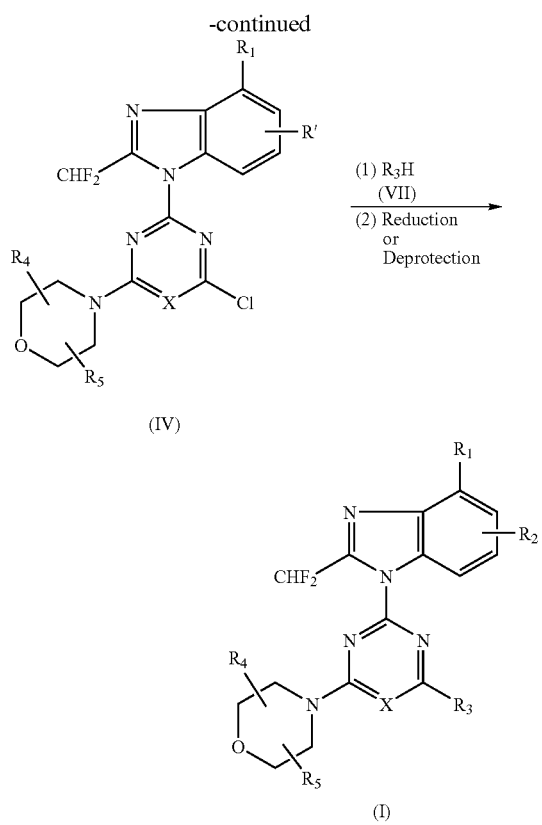

wherein $R_1$, $R_2$, $R_3$, $R_4$, $R_5$ and X are as defined above and R' represents hydrogen atom, amino or tert-butyldimethylsilyloxy.

Next, the respective production processes will be described.

1) Production Process (i) of Intermediate III:

Reaction Formula (i)

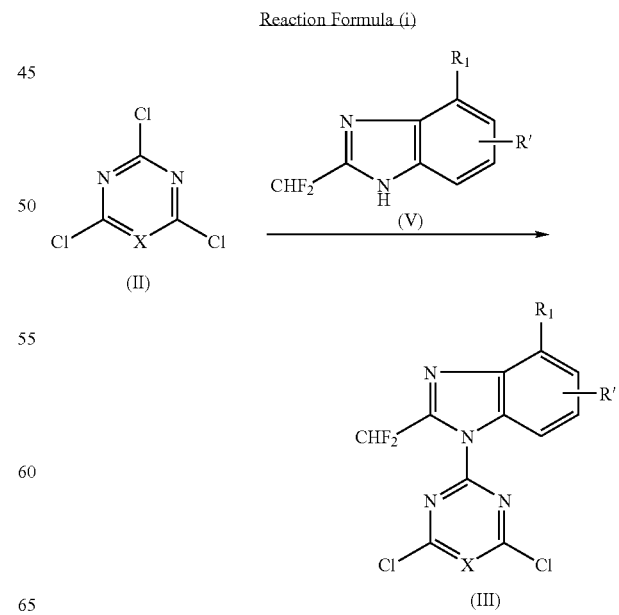

wherein $R_1$, R' and X are as defined above.

In a solvent, cyanuric chloride or 2,4,6-trichloro-pyrimidine (compound II) is reacted with benzimidazole compound (compound V) in the presence of hydrogen chloride trapping agent to obtain the intermediate III.

The hydrogen chloride trapping agent used in this reaction may be, for example, sodium hydroxide, potassium hydroxide, sodium carbonate, potassium carbonate, triethylamine or pyridine. The solvent used may be acetone, toluene, hexane, xylene, dioxane, tetrahydrofuran or dichloroethane or N,N-dimethylformamide (DMF).

In this reaction, 0.5–1.2 moles of the compound V is used per mole of the compound II in the presence of 0.5–2 moles of the hydrogen chloride trapping agent. The reaction is made at the temperature of −15° C.–−5° C. for 0.5–2 hours, and further at the room temperature for 5–50 hours.

It is to be noted that the compound V may be also used as the hydrogen chloride trapping agent.

2) Production Process (ii) of Intermediate IV

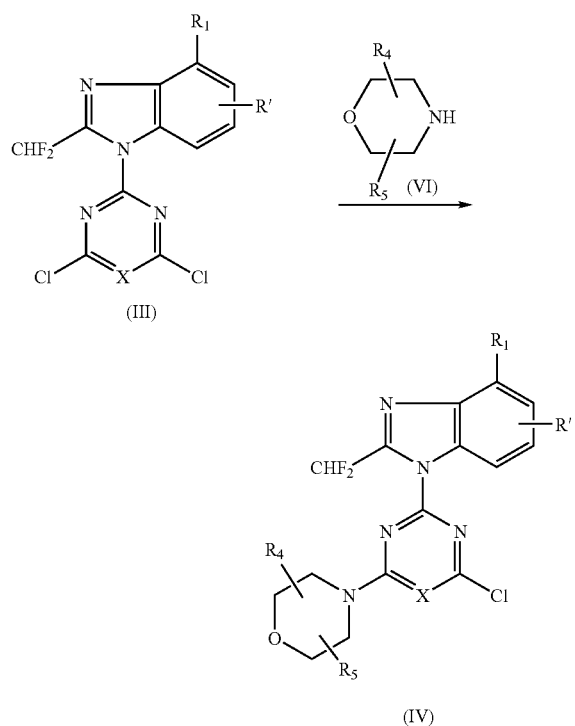

wherein $R_1$, $R_4$, $R_5$, R' and X are as defined above.

In the solvent, the intermediate III obtained in the above-mentioned production process (i) is reacted with morpholine compound (compound VI) in the presence of hydrogen chloride trapping agent to obtain the intermediate IV. The hydrogen chloride trapping agent used in this reaction may be the same as those in the above-mentioned production process (i). The solvent used may be DNF, acetone, toluene, xylene, dichloroethane or dichloromethane.

In this reaction, 0.5–1.2 moles of the compound VI is used per mole of the intermediate III and in the presence of 0.5–3 moles of the hydrogen chloride trapping agent. The reaction is made at the temperature of −5° C.–0° C. for 0.5–3 hours, and further at the room temperature for 5–50 hours.

It is to be noted that the compound VI may be also used as the hydrogen chloride trapping agent.

3) Production Process (iii) of the Compound I

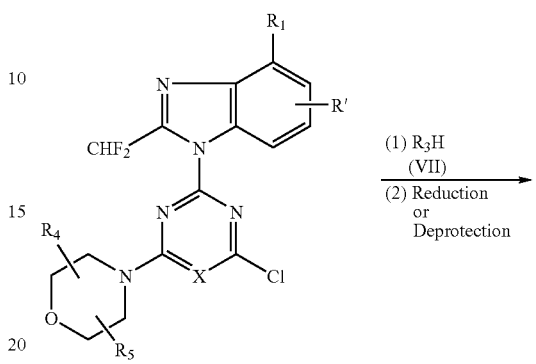

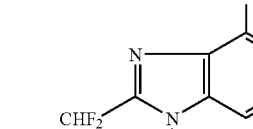

wherein $R_1$, $R_2$, $R_3$, $R_4$, $R_5$, R' and X are as defined above.

In the solvent, the intermediate IV obtained in the above-mentioned production process (ii) is reacted with $R_3H$ (compound VII) in the presence of hydrogen chloride trapping agent to obtain the compound I according to the present invention.

The hydrogen chloride trapping agent used in this reaction may be the same as those in the above-mentioned production process (i). The solvent used may be DMF, dimethyl sulfoxide (DMSO), xylene or dichloroethane.

In this reaction, 1–5 moles of $R_3H$ (compound VII) is used per mole of the intermediate IV at the temperature between room temperature and 140° C. for 0.1–16 hours. In the case of the reaction in the presence of the hydrogen chloride trapping agent, 1–5 moles of the hydrogen chloride trapping agent is used per mole of the intermediate IV. It is to be noted that the compound VII may be also used as the hydrogen chloride trapping agent.

In such production of the compound I and when the compounds VI and VII are the same, the production processes (ii) and (iii) may be carried out in a single step to obtain the compound I. In this case, the reaction conditions are as mentioned in the above with respect to the production process (ii) except that 2–10 moles of the compound VI or VII is used per mole of the compound III and that the reaction is made at the temperature of −10° C.–5° C. for 0.1–5 hours, and further at the temperature between room temperature and 120° C. for 3–50 hours.

When the compound V, VI or VII used in the production process (i), (ii) or (iii) has lower reactivity, it is preferable that the production process is carried out after treatment with sodium hydride. In the case of sodium hydride being used, 1.0–1.2 moles of sodium hydride is used per mole of the starting material (compound II, III or IV) in the production process.

When $R_1$ or $R_2$ is hydroxyl, the reaction is carried out, using benzimidazole compound with hydroxy protected by alkylsilyl group such as tert-butyldimethylsilyl according to ordinary method; in a final step, the protective group is removed to obtain the aimed compound. The compounds according to the present invention where $R_1$ is halogen atom and $R_2$ is hydroxyl may be obtained by halogenating, according to ordinary method, the compounds I similarly obtained in the above method and where $R_1$ is hydrogen atom and $R_2$ is hydroxyl.

The above-mentioned production processes (i), (ii) and (iii) may be carried out in any exchanged order. In such a case, the reaction conditions may be varied to an extent obvious to ordinary experts in the art.

The resultant products in the above-mentioned respective production processes may be separated and purified, as needs demand, by ordinary method such as extraction, condensation, neutralization, filtration, re-crystallization or column chromatography.

Acid-addition salts of the compounds I of the present invention may be prepared according to various methods well-known in the art. The appropriate acids used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

Next, antitumor activities of the compounds I of the present invention will be described. Numbers of the tested compounds in the tests 1 and 2 correspond to those in Examples referred to hereinafter.

Comparative compounds used were the following s-triazine-series antitumor agents or medicines for estrogen-dependent diseases:

Compound A: 2-(benzimidazol-1-yl)-4-(trans-2,3-dimethylmorpholino)-6-morpholinopyrimidine (a typical compound disclosed in the international publication WO99/05138)

Compound B: 2-(2-methylbenzimidazol-1-yl)-4,6-dimorpholino-1,3,5-triazine (a typical compound disclosed in the international publication WO99/05138)

Compound C: 2-(imidazol-1-yl)-4,6-dimorpholino-1,3,5-triazine (typical compound disclosed in the international publication WO93/17009)

Compound D: hexamethylmelamine (HMM)

Test 1

Used in the test were MCF-7 cells which were established from human breast cancer and were cultured routinely under the conditions of 37° C. and 5% $CO_2$, in MEM medium supplemented with 10% fetal calf serum, 25 mM of HEPES and 0.1 mg/ml of kanamycin. The MCF-7 cells in a logarithmic growth phase were treated with trypsin/EDTA to prepare single cell suspension adjusted to $4.0 \times 10^4$ cells/ml in MEM medium (supplemented with 10% fetal calf serum, 25 mM of HEPES and 0.1 mg/ml of kanamycin). Test compounds were dissolved in DMSO and diluted with RPMI 1640 medium (supplemented with 10% fetal calf serum, 25 mM of HEPES and 0.1 mg/ml of kanamycin) to a concentration of $2.0 \times 10^{-9} - 2.0 \times 10^{-4}$ M.

The cell suspension was filled in a 96-wells microplate at a rate of 0.1 ml per well and was cultured for 24 hours so as to make the cells adhered to the microplate. Then, it was added with 0.1 ml of the sample solution and cultured at 37° C. for 72 hours in 5% $CO_2$.

50% Growth inhibition concentrations ($GI_{50}$ µM) were calculated from growth inhibitions at various sample concentrations. The results are as shown in Table 1.

TABLE 1

| test compound | $GI_{50}$ (µM) |
| --- | --- |
| compound 1 | 0.07 |
| compound 2 | 0.08 |
| compound 3 | 0.27 |
| compound 5 | 0.06 |
| compound 6 | 0.08 |
| compound A | 2.2 |
| compound B | 3.7 |
| compound C | 20 |
| compound D | >100 |

The above test results clearly revealed that the compounds of the present invention exhibit by far superior antitumor activities on human breast cancer cells than the known comparative compounds A, B, C and D.

The compounds of the present invention were also effective in vitro tests using human non small cell lung cancer cells and human colonic cancer cells and therefore positively expected is application of the compounds according to the present invention on treatment of various human solid cancers.

Test 2

Mutant BALB/c nude mice were used for routine culture of 2-mm-square piece of human colonic cancer WiDr which was transplanted subcutaneously into left breast of each of the mice. The mice were separated for testing into groups each of five mice at the time of the tumor in its logarithmic growth phase. The samples prepared by dissolving test compounds in physiological saline solution or suspending them in 1% hydroxypropyl cellulose (HPC), using an agate mortar, were intraperitoneally administered at a rate of 200 mg/kg, once a day and six times a week in total, for two weeks. Major and minor axes of the tumor mass were measured on a daily basis to calculate tumor volume. The tumor volume at each measured day was divided by that at the start day of the sample administration to calculate relative tumor growth rate; and the relative tumor growth rate of the treated groups (T) and that of the control group (C) were used to calculate T/C (%) Cases where T/C (%) of the last day was less than 50% and U-assay of Mann-Whitney revealed significant difference with one-sided risk rate of 1% were judged to be effective (+). As a result, the compound according to the present invention was effective whereas the comparative compound A was ineffective.

Next, description will be made on ways of administration, formulations and dosage of the compounds of the present invention where they are applied to mammals, especially to human.

The compounds of the present invention may be administered orally or parenterally. In oral administration, the compounds may be in the formulation of tablets, coated tablets, powders, granules, capsules, microcapsules, syrups and the like; and in parenteral administration, in the formulation of injections which may include soluble freeze-drying formulation, suppositories and the like. In the preparation of these formulations, pharmaceutically acceptable excipient, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

The dosage for humans may depend on the condition of the disease to be treated, the age and weight of the patient and the like. A daily dosage for an adult may be in the range of from 100 to 1,000 mg and may be given in divided doses 2 or 3 times a day.

BEST MODE FOR CARRYING OUT THE INVENTION

Next, the present invention is more specifically illustrated with reference to the following Examples of the compounds. It is to be, however, noted that the present invention is not limited to these Examples.

EXAMPLE 1

2-(2-difluoromethyl-4-hydroxybenzimidazol-1-yl)-4-(2-hydroxymethylpyrrolidin-1-yl)-6-morpholinopyrimidine (Compound 1)

(1) 1.49 g (5.0 mmol) of 4-tert-butyldimethylsilyloxy-2-difluoromethylbenzimidazole dissolved in DMF (10 ml) was added with a solution of 2,4,6-trichloropyrimidine (0.91 g, 5.0 mmol) at room temperature, and further added with potassium carbonate (0.55 g) and stirred for 5 hours. The reaction solution was poured into water and extracted with ethyl acetate several times, washed with saturated saline solution and dried over anhydrous magnesium sulfate. The solvent was removed under reduced pressure and the residue was purified by silica gel column chromatography (n-hexane:ethyl acetate=8:1) to obtain 1.12 g (yield: 50%) of 2-(4-tert-butyldimethylsilyloxy-2-difluoromethylbenzimidazol-1-yl)-4,6-dichloropyrimidine.

(2) 386 mg (0.87 mmol) of the obtained 2-(4-tert-butyldimethylsilyloxy-2-difluoromethylbenzimidazol-1-yl)-4,6-dichloropyrimidine dissolved in DMF (6 ml) was added with 2-pyrrolidinmethanol (0.13 ml, 1.3 mmol) at room temperature, further added with potassium carbonate (179 mg) and stirred at room temperature for 30 minutes. The reaction solution was poured into water and extracted several times with ethyl acetate, washed with saturated saline solution and dried over anhydrous magnesium sulfate. The solvent was removed under the reduced pressure and the residue was purified by silica gel column chromatography (n-hexane:ethyl acetate=1:1) to obtain 291 mg (yield: 64%) of 2-(4-tert-butyldimethylsilyloxy-2-difluoromethyl-benzimidazol-1-yl)-4-(2-hydroxymethylpyrrolidin-1-yl)-6-chloropyrimidine.

(3) 281 mg (0.54 mmol) of the obtained 2-(4-tert-butyldimethylsilyloxy-2-difluoromethylbenzimidazol-1-yl)-4-(2-hydroxymethylpyrrolidin-1-yl)-6-chloropyrimidine added with morpholine (4.4 g, 50 mmol) was stirred at room temperature for 9 hours. The reaction solution was poured into water, extracted several times with ethyl acetate, washed with saturated saline solution and dried over anhydrous magnesium sulfate. The solvent was removed under the reduced pressure and the residue was purified by silica gel column chromatography (n-hexane: ethyl acetate=2:3) to obtain 216 mg (yield: 72%) of 2-(4-tert-butyldimethylsilyloxy-2-difluoromethylbenzimidazol-1-yl)-4-(2-hydroxymethylpyrrolidin-1-yl)-6-morpholinopyrimidine.

213 mg (0.38 mmol) of 2-(4-tert-butyldimethyl-silyloxy-2-difluoromethylbenzimidazol-1-yl)-4-(2-hydroxymethylpyrrolidin-1-yl)-6-morpholinopyrimidine dissolved in anhydrous THF (7 ml) was added with tetra-n-butylammoniumfluoride (0.4 ml, 1M THF solution) at room temperature and stirred for 30 minutes. The reaction solution was added with water, extracted several times with ethyl acetate, washed with saturated saline solution and dried over anhydrous magnesium sulfate. The solvent was removed under the reduced pressure and the residue was purified by silica gel column chromatography (n-hexane ethyl acetate=1:4) to obtain 101 mg (yield: 60%) of the titled compound as colorless crystals.

Melting point: 195–198° C.

NMR (CDCl$_3$) δ: 2.0–2.1 (4H, m), 3.4–4.0 (12H, m), 4.0–4.1 (1H, m), 4.3–4.4 (1H, m), 5.36 (1H, s), 6.85 (1H, d, J=8 Hz), 7.28 (1H, t, J=8 Hz), 7.58 (1H, brs), 7.58 (1H, t, J=54 Hz), 7.73 (1H, d, J=8 Hz)

MS m/z: 446(M$^+$)

EXAMPLE 2

2-(6-amino-4-chloro-2-difluoromethylbenzimidazol-1-yl)-4-(2,2-dimethylmorpholino)-6-morpholino-1,3,5-triazine (Compound 2)

(1) 500 mg (2.3 mmol) of 6-amino-4-chloro-2-difluoromethylbenzimidazole dissolved in acetone (50 ml) was added with 2,4-dichloro-6-morpholino-1,3,5-triazine (542 mg, 2.3 mmol) at −15° C. and further added with potassium carbonate (500 mg). The reaction mixture was gradually raised in temperature into room temperature and stirred at room temperature for 5 hours. The solvent was removed under the reduced pressure and the residue was purified by silica gel column chromatography (n-hexane ethyl acetate=1:4) to obtain 272 mg (yield: 28%) of 2-(6-amino-4-chloro-2-difluoromethylbenzimidazol-1-yl)-4-chloro-6-morpholino-1,3,5-triazine.

(2) 150 mg (0.36 mmol) of the obtained 2-(6-amino-4-chloro-2-difluoromethylbenzimidazol-1-yl)-4-chloro-6-morpholino-1,3,5-triazine dissolved in DMF (6 ml) was added with 2,2-dimethylmorpholine hydrochloride (150 mg, 1.0 mmol) at −15° C. and further added with potassium carbonate (500 mg). The reaction mixture was stirred at room temperature overnight. The reaction solution was poured into water, extracted several times with ethyl acetate, washed with saturated saline solution and dried over anhydrous magnesium sulfate. The solvent was removed under the reduced pressure and the residue was purified by silica gel column chromatography (n-hexane: ethyl acetate =1:2) to obtain 130 mg (yield: 73%) of the titled compound as colorless crystals.

Melting point: 238° C. (decomp.)

NMR (CDCl$_3$) δ: 1.27 (6H, s), 3.68 (2H, s), 3.7–3.9 (12H, m), 6.82 (1H, d, J=2.3 Hz), 7.42 (1H, dt, J=9.6 Hz, J=53 Hz), 7.50 (1H, d, J=2.3 Hz)

MS m/z: 494(M$^+$)

In accordance with the procedure of the Example 2, the following compounds were prepared from the corresponding starting materials.

2-(6-amino-4-chloro-2-difluoromethylbenzimidazol-1-yl)-4-(2-hydroxymethylpyrrolidin-1-yl)-6-morpholino-1,3,5-triazine (compound 3)

Melting point: 256° C. (decomp.)

NMR (CD$_3$OD-CDCl$_3$ (1:1)) δ: 1.9–2.2 (4H, m), 3.68 (2H, s), 3.5–4.0 (11H, m), 4.39 (1H, brs), 6.84 (1H, d, J=2.1 Hz) 7.58 (1H, t, J=53 Hz), 7.64 (1H, d, J=2.1 Hz)

MS m/z:480(M$^+$)

2-(6-amino-4-chloro-2-difluoromethylbenzimidazol-1-yl)-4-[methyl(1-methylpiperidine-4-yl)amino]-6-morpholino-1,3,5-triazine (compound 4)

Melting point: 194° C. (decomp.)

NMR (CD$_3$OD-CDCl$_3$ (1:1)) δ: 1.3–1.5 (2H, m), 1.8–2.1 (4H, m), 2.35 (3H, s), 2.9–3.2 (3H, m), 3.21 (3H, s), 3.5–3.8 (8H, m), 6.84 (1H, d, J=2.2 Hz), 7.49 (1H, t, J=53 Hz), 7.80 (1H, d, J=2.2 Hz)

MS m/z:507(M$^+$)

2-(2-difluoromethyl-4-hydroxybenzimidazol-1-yl)-4-(2-hydroxymetylpyrrolidin-1-yl)-6-morpholino-1,3,5-triazine (compound 5)

Melting point: 245° C. (decomp.)

NMR (CDCl$_3$) δ: 1.9–2.1 (4H, m), 3.5–4.0 (12H, m), 4.7–4.8 (1H, m), 5.1–5.3 (1H, m), 6.89 (1H, d, J=9 Hz), 7.30 (1H, t, J=9 Hz), 7.50 (1H, brs), 7.55 (1H, t, J=54 Hz), 7.83 (1H, d, J=9 Hz)

MS m/z:447(M$^+$)

2-(2-difluoromethyl-5-hydroxybenzimidazol-1-yl)-4,6-dimorpholino-1,3,5-triazine

Melting point: >250° C.

NMR (CDCl$_3$) δ: 3.8–4.0 (16H, m), 7.01 (1H, d, J=9 Hz), 7.30 (1H, s), 7.54 (1H, t, J=53 Hz), 8.19 (1H, d, J=9 Hz)

MS m/z: 433(M$^+$)

EXAMPLE 3

2-(4-chloro-2-difluoromethyl-5-hydroxybenzimidazol-1-yl)-4,6-dimorpholino-1,3,5-triazine (compound 6)

In accordance with the procedure of the Example 2, 433 mg (1.00 mmol) of 2-(2-difluoromethyl-5-hydroxybenzimidazol-1-yl)-4,6-dimorpholino-1,3,5-triazine was obtained. 433 mg (1.00 mmol) of the obtained compound dissolved in chloroform (10 ml) was added with N-chlorosuccinimido (400 mg, 3.0 mmol) and stirred at 60° C. for 1 hour. The reaction solution was poured into water and extracted several times with chloroform, washed with saturated saline solution and dried over anhydrous magnesium sulfate. The solvent was removed under the reduced pressure and the residue was purified by silica gel column chromatography (chloroform:methanol=99:1) to obtain 189 mg (yield: 44%) of the titled compound as colorless crystals.

Melting point: >250° C.

NMR (CDCl$_3$) δ: 3.7–3.9 (16H, m), 5.63 (1H, s), 7.15 (1H, d, J=9 Hz), 7.51 (1H, t, J=53 Hz), 8.14 (1H, d, J=9 Hz)

MS m/z: 467(M$^+$)

INDUSTRIAL APPLICABILITY

The compounds of the present invention exhibit apparently by far strong antitumor activities with no aromatase inhibitory activities in comparison with conventional s-triazine and pyrimidine derivatives and can be applied to treatment on solid cancers.

What is claimed is:

1. A heterocyclic compound represented by the formula I or a pharmaceutically acceptable salt thereof:

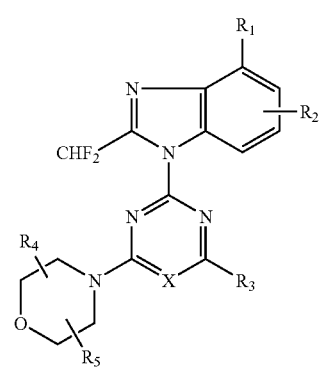

wherein
X represents a nitrogen atom or CH;
R$_1$ represents a halogen atom or hydroxyl;
R$_2$ represents a hydrogen atom, hydroxyl or amino;
R$_3$ represents morpholino (which may be substituted with one or two C$_1$–C$_6$ alkyl), pyrrolidinyl (which may be substituted with hydroxy C$_1$–C$_6$ alkyl), or NR$_6$R$_7$ [wherein R$_6$ represents C$_1$–C$_6$ alkyl and R$_7$ represents piperidinyl (which may be substituted with C$_1$–C$_6$ alkyl)];
R$_4$ and R$_5$ each independently represent a hydrogen atom or C$_1$–C$_6$ alkyl;
with the proviso that R$_2$ is hydrogen atom and R$_3$ is pyrrolidinyl (which may be substituted with hydroxy C$_1$–C$_6$ alkyl) when R$_1$ is hydroxyl.

2. The compound according to claim 1, wherein R$_1$ is chloro.

3. The compound according to claim 1, wherein R$_1$ is chloro and R$_2$ is amino.

4. The compound according to claim 1, wherein R$_1$ is chloro, R$_2$ is amino, R$_3$ is dimethylmorpholino, R$_4$ and R$_5$ each are hydrogen atom and X is nitrogen atom.

5. The compound according to claim 1, wherein R$_1$ is chloro and R$_2$ is hydroxyl.

6. The compound according to claim 1, wherein R$_1$ is chloro, R$_2$ is hydroxyl, R$_3$ is morpholino, R$_4$ and R$_5$ each are hydrogen atom and X is nitrogen atom.

7. The compound according to claim 1, wherein R$_1$ is hydroxyl, R$_2$ is hydrogen atom and R$_3$ is pyrrolidinyl (which may be substituted with hydroxymethyl).

8. The compound according to claim 1, wherein the compound represented by the formula I is:
2-(2-difluoromethyl-4-hydroxybenzimidazol-1-yl)-4-(2-hydroxymethylpyrrolidin-1-yl)-6-morpholinopyrimidine,
2-(6-amino-4-chloro-2-difluoromethylbenzimidazol-1-yl)-4-(2,2-dimethylmorpholino)-6-morpholino-1,3,5-triazine,
2-(6-amino-4-chloro-2-difluoromethylbenzimidazol-1-yl)-4-(2-hydroxymethylpyrrolidin-1-yl)-6-morpholino-1,3,5-triazine,
2-(6-amino-4-chloro-2-difluoromethylbenzimidazol-1-yl)-4-[methyl(1-methylpiperidin-4-yl)amino]-6-morpholino-1,3,5-triazine,
2-(2-difluoromethyl-4-hydroxybenzimidazol-1-yl)-4-(2-hydroxymethylpyrrolidin-1-yl)-6-morpholino-1,3,5-triazine, or
2-(4-chloro-2-difluoromethyl-5-hydroxybenzimidazol-1-yl)-4,6-dimorpholino-1,3,5-triazine.

9. The compound according to claim 1, wherein the compound represented by the formula I is 2-(2-difluoromethyl-4-hydroxybenzimidazol-1-yl) -4-(2-hydroxymethylpyrrolidin-1-yl)-6-morpholino-1,3,5-triazine.

10. A pharmaceutical composition comprising:
the compound of claim 1, and
at least one pharmaceutically acceptable diluent or carrier.

11. A method for treating human breast cancer, comprising administering to a subject in need thereof an effective amount of the compound of claim 1 or a pharmaceutically acceptable salt thereof.

12. A method for treating human lung cancer, comprising administering to a subject in need thereof an effective amount of the compound of claim 1 or a pharmaceutically acceptable salt thereof.

13. A method for treating human colon cancer, comprising administering to a subject in need thereof an effective amount of the compound of claim 1 or a pharmaceutically acceptable salt thereof.

14. The compound of claim 1, wherein X is a nitrogen atom.

15. The compound of claim 1, wherein X is CH.

16. The compound of claim 1, wherein $R_1$ represents a halogen atom.

17. The compound of claim 1, wherein $R_2$ represents a hydrogen atom.

18. The compound of claim 1, wherein $R_2$ represents hydroxyl.

19. The compound of claim 1, wherein $R_2$ represents amino.

20. The compound of claim 1, wherein $R_3$ represents morpholino (which may be substituted with one or two $C_1$–$C_6$ alkyl).

21. The compound of claim 1, wherein $R_3$ represents pyrrolidinyl (which may be substituted with hydroxy $C_1$–$C_6$ alkyl).

22. The compound of claim 1, wherein $R_3$ represents $NR_6R_7$ [wherein $R_6$ represents $C_1$–$C_6$ alkyl and $R_7$ represents piperidinyl (which may be substituted with $C_1$–$C_6$ alkyl)].

* * * * *